United States Patent
John et al.

(10) Patent No.: US 8,538,552 B2
(45) Date of Patent: Sep. 17, 2013

(54) ADAPTIVE CONDUCTIVE LEAD SYSTEMS

(75) Inventors: Michael Sasha John, Larchmont, NY (US); David R. Fischell, Fair Haven, NJ (US)

(73) Assignee: Angel Medical Systems, Inc., Fair Haven, NJ (US)

(*) Notice: Subject to any disclaimer, the term of this patent is extended or adjusted under 35 U.S.C. 154(b) by 1239 days.

(21) Appl. No.: 11/970,781

(22) Filed: Jan. 8, 2008

(65) Prior Publication Data

US 2008/0167701 A1   Jul. 10, 2008

Related U.S. Application Data

(60) Provisional application No. 60/879,367, filed on Jan. 9, 2007.

(51) Int. Cl.
*A61N 1/00* (2006.01)

(52) U.S. Cl.
USPC .......................................................... 607/116

(58) Field of Classification Search
USPC ......... 607/115–132; 600/373–381; 174/68.1
See application file for complete search history.

(56) References Cited

U.S. PATENT DOCUMENTS

| | | | |
|---|---|---|---|
| 3,265,638 A | 8/1966 | Goodman et al. | |
| 3,658,726 A | 4/1972 | Mühl | |
| 3,989,050 A | 11/1976 | Buchalter | |
| 3,998,215 A | 12/1976 | Anderson et al. | |
| 4,016,869 A | 4/1977 | Reichenberger | |
| 4,406,827 A | 9/1983 | Carim | |
| 4,845,457 A | 7/1989 | Nakanishi | |
| 5,007,435 A | 4/1991 | Doan et al. | |
| 5,075,038 A | 12/1991 | Cole et al. | |
| 5,099,855 A | 3/1992 | Yount | |
| 5,143,071 A | 9/1992 | Keusch et al. | |
| 5,178,143 A | 1/1993 | Kwak et al. | |
| 5,348,686 A | 9/1994 | Vyas | |
| 5,458,630 A | 10/1995 | Hoegnelid et al. | |
| 5,507,787 A * | 4/1996 | Borghi ............................ | 607/37 |
| 5,539,039 A | 7/1996 | Kwak et al. | |
| 5,645,062 A | 7/1997 | Anderson et al. | |
| 5,817,016 A | 10/1998 | Subramaniam | |
| 6,012,457 A | 1/2000 | Lesh | |
| 6,529,778 B2 | 3/2003 | Prutchi | |
| 6,591,143 B1 | 7/2003 | Ekwall | |
| 6,620,159 B2 | 9/2003 | Hegde | |
| 7,065,411 B2 | 6/2006 | Verness | |
| 7,127,294 B1 * | 10/2006 | Wang et al. ..................... | 607/36 |

OTHER PUBLICATIONS

Liem LK, et al.; "The patch clamp technique"; Neurosurgery; 1995; 36:382-392.

(Continued)

*Primary Examiner* — Eric D. Bertram
*Assistant Examiner* — Elizabeth K So
(74) *Attorney, Agent, or Firm* — Rosenberg, Klein & Lee

(57) ABSTRACT

The invention describes fluid-based lead systems. The fluid-based leads may be used for sensing from, and stimulating of, human tissue. The fluid-based leads can be used to transfer signals between two locations. The fluid-based leads offer advantages when communicating signals along their length since the leads may be safely used in magnetic environments and offer increased elastic characteristics which are less prone to breakage. The leads can be used externally or with implantable devices, such as those used to monitor, and deliver therapy during the treatment of medical disorders such as cardiac and neurological disorders.

16 Claims, 5 Drawing Sheets

(56) References Cited

OTHER PUBLICATIONS

Lipton MJ, et al.; "A conductive catheter to improve patient safety during cardiac catheterization"; Circulation; Dec. 1978; 58(6):1190-1195.

Neher E, et al.; "Noise analysis of drug induced voltage clamp currents in denervated frog muscle fibres"; J Physiol; Jul. 1976; 258(3):705-729.

Ream AK, et al.; "Reduced risk of cardiac fibrillation with use of a conductive catheter"; Ann Biomed Eng; Sep. 1977; 5(3):287-301.

* cited by examiner

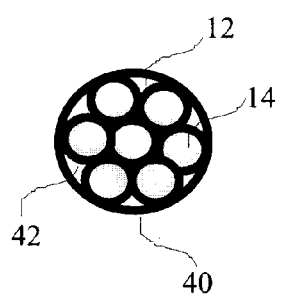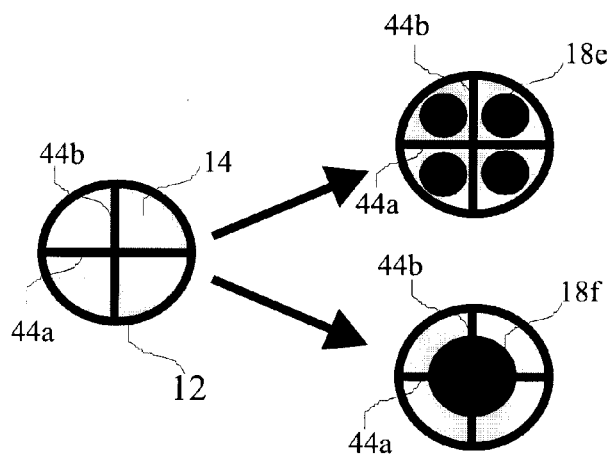
FIG 4A  FIG4B
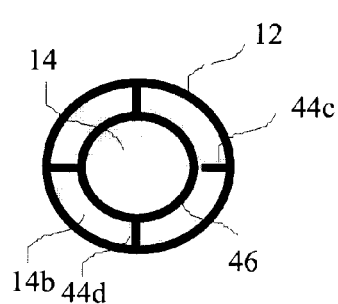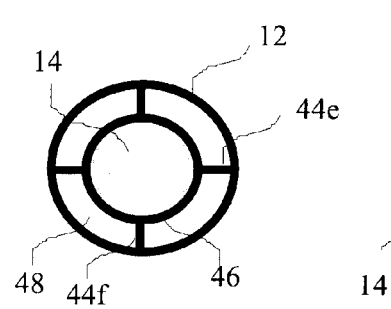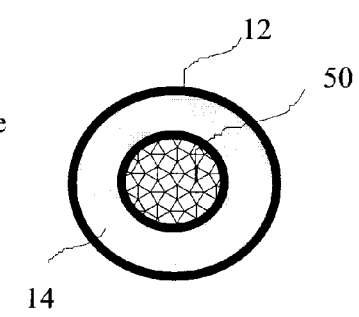
FIG 4C  FIG 4D  FIG4E

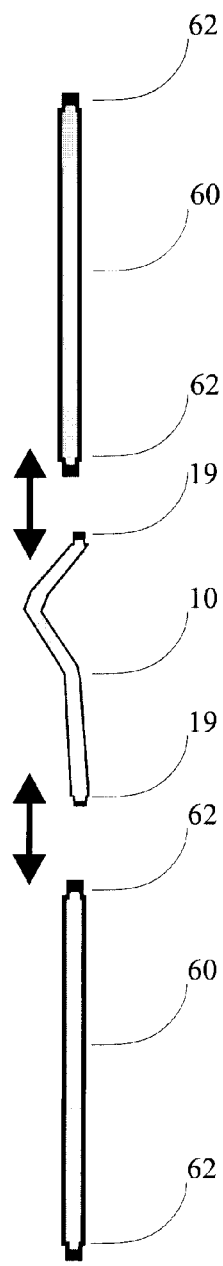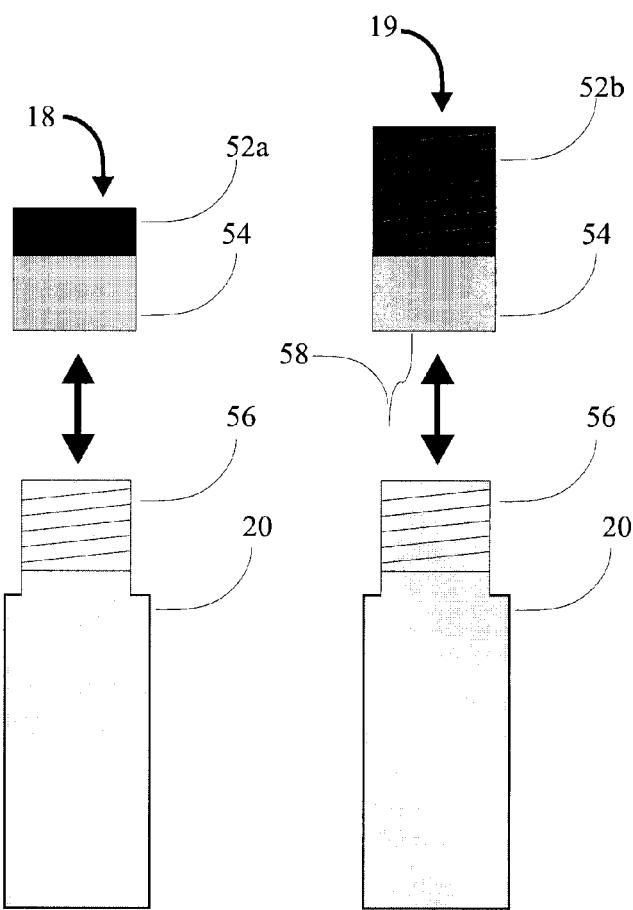
FIG 5　　　FIG 6A　　　FIG6B

ADAPTIVE CONDUCTIVE LEAD SYSTEMS

CROSS REFERENCE TO RELATED APPLICATIONS

This application claims priority of U.S. application Ser. No. 60/879,367 filed Jan. 9, 2007, entitled "Adaptive Conductive Lead Systems".

BACKGROUND

This invention is in the field of sensing of biological signals and also includes electrical communication between implanted devices, and between these devices and their sensors and stimulators. The invention also relates to leads used especially during medical procedures that require the use of magnetic fields.

Implantable medical devices having sensing and stimulation capacities are currently used in treatment of a wide array of medical disorders including, for example, neurological and cardiac abnormalities. In order to implement sensing and stimulation the implanted devices normally have leads which permit electrical communication between the device and the distal tip of the lead at which sensing or stimulation occurs. The leads are often comprised of one or more wires ("filars"), which may be straight or braided. Alternatively, wires may be replaced or wrapped within a mesh which is metallic-based or metallic-coated. Regardless of design, while significant efforts have been made to deter post-implantation breakage within the implanted leads this still occurs due to bending, kinking, and repetitive stress forces which occur during normal activity by the patient. Further, while flexible, the current leads are not configured to allow stretching.

Known methods of addressing this problem include U.S. Pat. No. 7,065,411 to Verness entitled "Electrical medical leads employing conductive aerogel" (the '411 patent) which describes implementing a conductive aerogel and a metallic lead within an insulative sheath. An areogel is nanoscle mesoporous material, containing very little mass (e.g., 99.8% air and 0.2% matter). The '411 patent is a relatively high-tech solution which has culminated from failure of more basic approaches as is reviewed therein. For example, U.S. Pat. No. 5,007,43 describes coiled wire conductors that are parallel-wound and separately coupled between a proximal and distal connector. Similar prior art embodiments describe various embodiments such as leads comprising coiled wire lumens, multi-filar leads embedded in various types of sheaths, leads using both serial and parallel configurations, leads with stranded wires, and the like. The '530 application also describes other known strategies for increasing life and durability of leads, such as multiple concentric-lumen designs wherein an interior lumen houses the conductive filar, and provides mobility within an outer sheath when movement occurs. Further, concentric lumen and their respective components may be bathed in a liquid silicone fluid or other lubricating medium in order to deter the risk of tension and breakage. Additionally, the conductive filer may be fitted within a conductive silicone rubber tube to provide a redundant system which is able to compensate for fracture and reduced conductivity of the wire filar.

It is also known that leads which are either implanted or which are external to the patient and which contain metallic wire conductors may show unwanted characteristics when submitted to magnetic fields of the type that may be used during certain medical procedures. For example, during medical imaging procedures which use strong magnetic fields such as magnetic resonance imaging (MRI) procedures, including functional MRI (fMRI) procedures, wire-based leads may be prone to induced currents which cause unwanted side-effects, such as thermal or electrical generation, which are a large safety issue for the patient. These side-effects can be harmful to the patient and may also cause distortion of the data obtained during the imaging procedure. It would be preferable to avoid these unwanted side-effects.

Catheters, made of either conductive or non-conductive materials, have been investigated using catheters containing either saline or guidewires (Ream et al, 1977; Lipton et al 1978). These catheters were used for experimental purposes in order to investigate issues of patient safety related to cardiac catheterization, and in order to examine the risk of spurious fibrillation caused by leakage currents induced from external equipment. In these studies, the saline within the catheters was not used for sensing or stimulation, but rather for manipulation of the leakage currents.

In U.S. Pat. No. 6,620,159, entitled "conductive expandable electrode body and method of manufacturing the same", to Hegde, there is described an ablation catheter which contains a ballooned electrode assembly. The catheter both transmits electrical energy and also establishes the radius of a balloon using an electroconductive fluid which is pumped into the balloon. The '159 patent describes a number advantages over U.S. Pat. No. 6,012,457, to Lesh, which, in turn, describes a similar device wherein the electroconductive fluid is further used as an interface between the catheter's distal tip and the surrounding tissue in order to transmit the electrical energy to surrounding tissue. In U.S. Pat. No. 6,529,778 entitled "Fluid-phase electrode lead" summarizes devices which provide fluid to the electrode-tissue interface and discloses a fluid-phase electrode which utilizes a vacuum to anchor the distal tip to the target tissue.

Saline filled glass electrodes are often used as micro-electrodes when recording intracellular activity and membrane dynamics using patch-clamp techniques and when regulating current or voltage using clamp techniques (e.g. Neher & Sakmann 1976). The goal of a voltage clamp experiment is to measure membrane current. To do this, one monitors the membrane voltage and injects current to attain and maintain the desired voltage: a voltage-clamp amplifier and electrode must be able to: 1) measure voltage and 2) pass current in order to regulate the cellular voltage Patch-clamp techniques allow cellular function and regulation to be studied at a molecular level by observing currents through individual ionic channels. The electrodes used in clamp-type experiments are never flexible or subjected to magnetic fields as would occur during an MRI procedure.

U.S. Pat. No. 6,591,143 describes a "bending sensor for an implantable lead." The sensor has an electrical resistance that various depending on how much the sensor is bent. The variable resistance is effected by a sending a current through fluid filled cavities and comparing the voltage drop across different cavities.

U.S. Pat. No. 5,458,630, to Hoegnelid et al. describes a "medical electrode device having a non-gaseous fluid conductor". The conductor employs a non-gaseous, non-metallic electro-conductive gel which transmits electrical signals along the length of the lead.

SUMMARY OF THE INVENTION

Various types of flexible and/or stretchable leads are described. According to one embodiment, the lead comprises a sheath which includes a fluid conductive element that is configured for transmitting signals along at least a portion of the length of the lead. The lead is less prone to breakage and kinking due to the use of novel features such as a support structure which may be realized as an internal lattice. The lead may also contain one or more solid conductive elements along a portion of the lead length. The lead may be realized using one or more lumen which may be concentric or realized in series, and the individual lumen, and the material contained within these, may have distinct properties. When the lead is implanted it can increasingly conform to a patient's movement due to increased flexibility. Whether external or internally positioned, the leads offer advantages when used in an MRI environment, for example, to record the electroencephalogram (EEG) in that environment.

When one or more fluid compartments are defined these may be either non-pressurized or pressurized. By providing compartments, pressures due to bending of the lead can be isolated to a particular portion of the lead, rather than causing fluid to flow away from the source-point of the pressure. This is one manner disclosed for maintaining minimum and maximum pressures levels within a particular range, as compared to a design in which the internal lumen forms a single compartment along the length of the lead. Other methods include various types of endoskeleton and exoskeleton structures as well as local pressure inducing structures.

Especially when the leads are used in external applications such as MRI environments, the fluid based leads may be constructed with translucent portions and may also contain a dyed fluid which can be visually inspected in order to ensure fluid integrity. Other, non-visual testing methods are described to increase the likelihood of at least a specified level of conductive performance. The lead can be constructed with a width and length that is determined by the signal transmission characteristics which will be required during its use.

In one embodiment, the terminals of the leads are designed to permit the lead to serve as a junction between two other conventional leads, or as a flexible terminal member of a conventional lead which may serve as a sensor, or which may be attached to a sensor or to a medical device.

BRIEF DESCRIPTION OF THE DRAWINGS

For the purpose of illustrating the invention and its advantages, there is provided a detailed description and accompanying drawings of embodiments which are presently preferred, it being understood that the invention is not intended to be limited to the precise arrangements and instruments shown, and wherein:

FIG. 4A is a schematic representation illustrating a multi-lead configuration housed in an external sheath;

FIG. 4B is a schematic representation illustrating a lead comprised a fluid compartment and an intra-lead support matrix, and illustrating a distal tip element having 4 independent connectors independently connected to the internal lumen for providing 4 independent lead channels (top right), or a signal connector for redundant communication (bottom right);

FIG. 4C is a schematic representation illustrating a lead comprising concentric fluid compartments and a supporting matrix;

FIG. 4D is a schematic representation illustrating a lead comprised an internal fluid compartment and an exoskeleton matrix separating this compartment from the external sheath;

FIG. 4E is a schematic representation illustrating a lead comprised a fluid compartment and an intra-lead rod matrix for adding rigidity and conductivity, which may be made of conductive or non-conductive material;

FIG. 5 is a schematic representation illustrating 2 conventional leads which are configured to be connected to a fluid-based lead;

FIG. 6A is a schematic representation illustrating a fluid-based lead having a distal tip element connector which is affixed to the terminal portion of the lead using a threaded section; and, FIG. 6B is a schematic representation illustrating a lead having a distal tip element connector which is affixed to the terminal portion of the lead using a threaded section and the connector is also threaded for connecting to a device or to a conventional lead that has been modified to accept this connector.

DETAILED DESCRIPTION OF THE PREFERRED EMBODIMENTS

The definitions of terms written in this specification shall be consistent with the context in which the terms appear and the ordinary broad meaning of such terms as would be understood by practitioners of ordinary skill in the arts relevant to the invention; notwithstanding that, some exemplary definitions (which are illustrative but shall not be considered limiting) are included at the end of the specification.

Figures 1A, 1B, 1C, 1D:
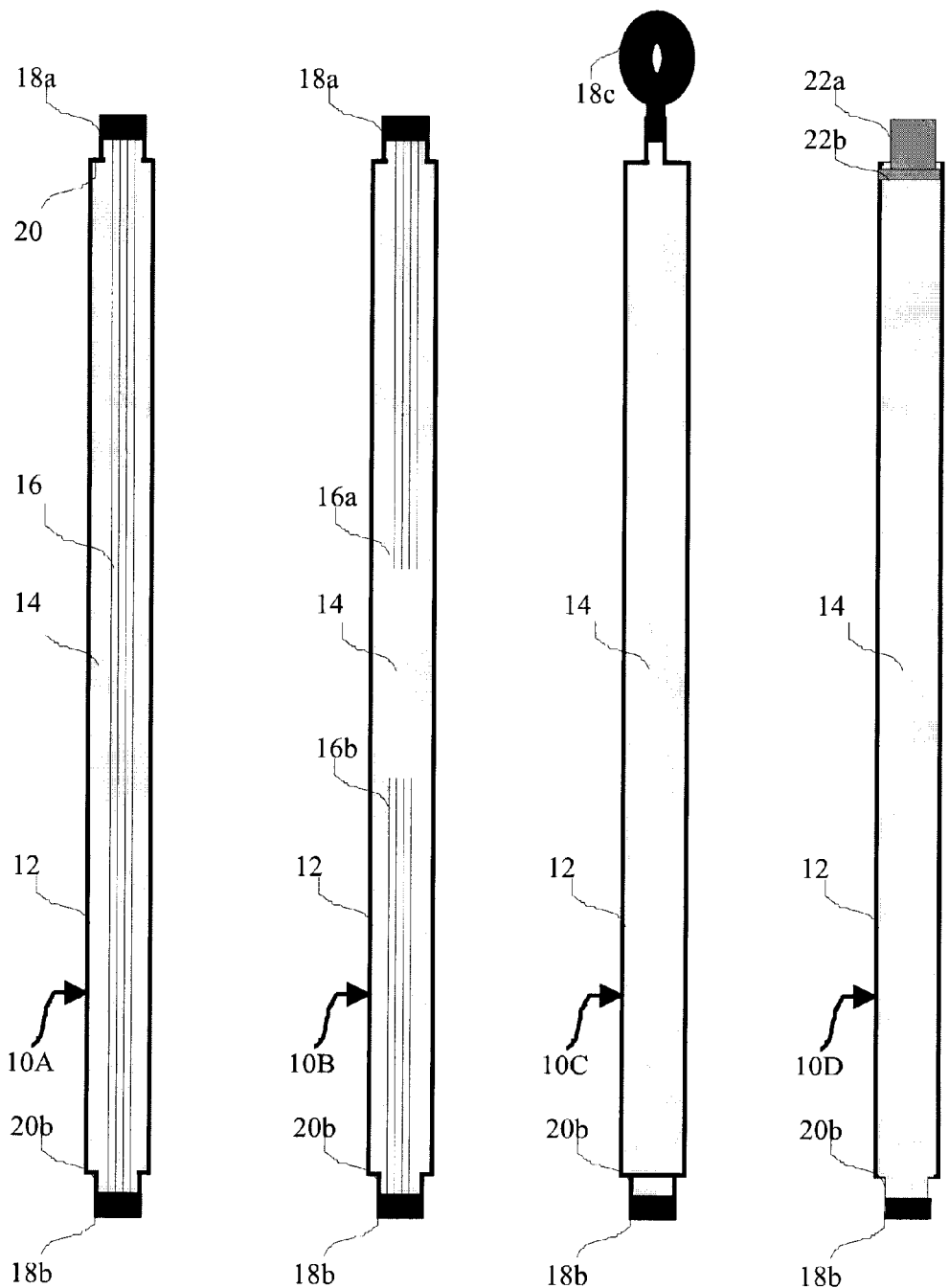
FIG. 1A shows an embodiment of the invention in which a lead contains a solid conductive element and a fluid conductive element.
FIG. 1B shows an alternative embodiment of the lead system of FIG. 1A in which two solid conductive elements are separated by a gap and a fluid conductive element is provided for conducting a signal across the gap.
FIG. 1C is a schematic representation illustrating a lead comprised solely of a fluid conductive element and also having a distal lead connector configured for sensing scalp EEG.
FIG. 1D is a schematic representation illustrating a lead comprised solely of a fluid conductive element and also having a distal lead connector that is configured as a conductive gel cap.

FIG. 1A shows an embodiment of the adaptive conductive lead (ACL) 10A which comprises a lead body 12, which is some form of sheath, tube, or liner which is approximately non-conductive, at least on its outside surface, and which contains fluid conductive element (FCE) 14 comprising a relatively electrically conductive and flexible medium such as an electrolytic gel or other type of electroconductive fluid. The body 12 can be made from a vinyl, rubber, plastic, or other flexible/elastic material and may be translucent, transparent or opaque. The lead body 12 preferably has a cylindrical shape but may also be realized with other shapes, such as a flattened or tape-like shape similar to leads used for neuro-stimulation. The lead body 12 also houses a solid conductive element (SCE) 16 which may be an electro-conductive metallic conductor such as a wire. In this embodiment, the SCE 16 connects to a distal lead connector 18a and to a proximal lead connector 18b and communicates electrical signals therebetween. The SCE 16 may also be a braided wire, or a metallic-based or metallic-coated mesh. The body 12 contains a distal terminal portion 20a and a proximal terminal portion 20b, which in FIG. 1A are simply circular indentations that conform to the distal lead connector 18a and proximal lead connector 18b, respectively. The lead connectors 18 can be connected to the terminal portions 20 by being formed therein, using a glue or epoxy, using a mechanical securing means, by being partially inserted therein so that they are snuggly held, or by other securing strategy (e.g., 'lock-and-key' type implementation, screwing into a threaded inner surface, etc.). The lead 10A offers advantages over conventional leads because if the SCE 16 suffers an insult such as a partial or complete breakage, the FCE 14 will enable the electrical connection between the two lead connectors 18 to be maintained.

In one embodiment, the SCE 16 can be comprising a conductive powder, such as fine aluminum dust. A powder conductive element PCE is a particular embodiment of an SCE 16 and may be comprising a loose or compacted powder. For example, the PCE may be poured into a lead body 12 and packed tightly until the space between the proximal and distal ends provides continuous electrical continuity. In an alternative embodiment a fluid-powder conductive element FPCE can be used wherein the FPCE 15 is comprising a mixture that is mainly fluid (e.g., 60% fluid and 40% powder) or mainly powder (e.g., 40% fluid and 60% powder) and may be best thought of as a type of SCE in the prior case and a PCE in the latter case, respectively. One preferred embodiment which provides conductivity similar to that found using a wire lead comprises a gel suspension of 80% powder a 20% gel.

FIG. 1B shows additional embodiment of the invention that is a lead 10B in which rather than a single SCE 16 there are at least two distinct SCE segments which in this case are a distal metallic conductor segment 16a and a proximal metallic conductor segment 16b. The fluid conductive element 14 extends along the entire length of the lead 10B. This embodiment is termed an "interleaved" embodiment because electrical communication between the terminal portions 20 requires at least 2 interleaved conductive elements. When the body 12 of the lead is flexible or stretchable, the lead may be twisted and stretched while electrical communication between the lead connectors 18a, 18b is maintained. Interleaved leads are a type of 'sequential component' embodiment where portions of adjacent components are characterized by overlap. In this case the lead for communicating electrical signals comprises a sheath, an electroconductive proximal lead connector, an electroconductive distal lead connector; and at least two serially positioned conductive elements which have some degree of overlap and which are configured to transmit signals between the proximal and distal lead connectors. The gap between the SCEs 16a, 16b may be less than, for example, a quarter inch, when the lead is not stretched. It is possible that when the lead is stretched beyond some amount by the patient that the electrical connection is acutely broken, and the connection is re-established when the lead returns to a relatively un-stretched position.

FIG. 1C shows additional embodiment of the invention that is a lead 10C in which rather than also including a SCE 16 there is a single FCE 14 connecting the lead connectors 18a, 18b of the terminal portions 20. When this lead is used external to the patient, then lead 10C also contains a lead connector 18c which is configured as a cup electrode which may be plated with a silver or gold alloy such as that commonly utilized in recording scalp electrical recordings known as the "electroencephalogram". The other end of the lead can have a connector which can be configured for connection to an EEG head-box (e.g., can have a hospital-grade female-type connector). In order to compensate for any increased impedance which may characterize certain types of fluid based conduits, the input impedance of a pre-amplifier in the EEG head-box may be increased so that it is still, for example, 100 times that of the that which occurs between the electrode and subject. This type of lead may offer advantages when used in environments with large magnetic fields.

FIG. 1D shows additional embodiment of the invention that is a lead 10D in which there is a single FCE 14 connecting the lead connectors 18 of the terminal portions 20. Lead 10D also contains a lead connector which is configured with a gel cap 22a and gel cap connector 22b. The gel cap 22a is a non-metallic connector such as that made by Physiometrix which is described in U.S. Pat. No. 5,817,016 to Subramaniam. The gel cap, and variations of the components of the gel cap, can be used to establish electrical contact with the conductive fluid in the lead. The gel cap is an electroconductive medium, which offers benefit over metallic lead because it will not generate thermal energy when a current is applied or induced due to an internal field or an external field such as a magnetic field. When implanted, it may also not suffer some of the metal-tissue issues of conventional electrode contacts. The gel cap 22a may be affixed to the distal terminal portion 20a of the lead body 12 by any number of mechanical or physical means (e.g. attachment component, glue, pressure, complementary physical conformation) and in this example a gel cap connector 22b conforms to the shape of the distal terminal portion 20a and provides electrical communication between the gel cap 22a and the internal FCE 14. A gel cap connector 22b can also be made of a rigid gel, or can be a plastic or metal component, although non-metallic embodiment is preferred when the issue of magnetic fields is relevant (e.g., when the lead is an external lead that is used acutely to record EEG during an fMRI procedure).

Figure 2A:
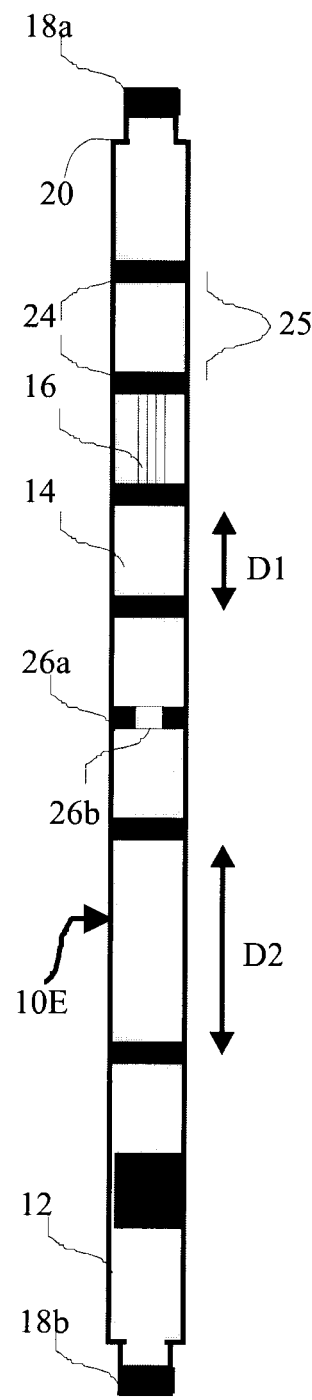
FIG. 2A is a schematic representation illustrating a lead comprising conductive fluid compartments, conductive spacers, and a solid conductive element.

FIG. 2A shows an additional embodiment of the invention that is a lead 10E in which a "serial" embodiment is shown. In this embodiment at least one metallic spacer 24 is used to create conducting compartments 25. Each conducting compartment can contain only an FCE 14, or can contain SCE 16 instead of, or in addition to the FCE 14. When a plurality of two or more metallic spacers 24 are used, these can be evenly distributed along the length of the lead body 12, can have unique separations as indicated by D1 and D2 in FIG. 2A, where D2 is larger than D1, or can exist only in a portion of the length of the lead 10E. The lead 10E also contains a metallic spacer 26a having a partition or gap 26b that is configured to permit the FCE 14 to travel between adjacent conducting compartments 25 so that changes in pressure or suction (i.e. negative pressure) cause a redistribution of the FCE 14 to accommodate change in the lead body which occur due to patient movement or other deforming force. The gap 26b can be made small so that acute flow-rate of the FCE between compartments 25 is dampened. The metallic spacers 24, 26 provide a number of advantages. Firstly, the distance between spacers 24, 26 can be adjusted in order to adjust the rigidity of the lead body 12, wherein more closely spaced spacers 24, 26 provide more rigidity. Secondly, the spacing between the spacers 24, 26 can serve to attenuate electrical phenomena (e.g., standing waves, capacitance values, induced filtering of signals) associated with electrical conductance which may cause interference, constrainment, or modification of the electrical signals that are transmitted across the lead body. Thirdly, the spacers 24, 26 can serve to physically constrain (support outward radial force to) the inner circumference of the lead body due to forces of inward compression which can occur, for example, due to stretching of the terminal portions in opposite directions. The risk of disruption of the FCE 14 due to kinking is thereby minimized. Fourthly, the spacers 24, 26 deter the cross sectional area of the FCE 14 from being reduced to less than a selected amount, due to bending or stretching, in order to preserve the resistance of the signal transmission below a selected level. In addition to the SCE 16 which is shown, multiple SCEs can be utilized in parallel in order to increase rigidity, conduction, and dependability of the lead. The SCE 16 may also comprise electronic components such as one or more diodes or resistors (or materials that create similar electrical results) that may be implemented to control the characteristics of the signal conduction. The spacers 24, 26 shown in FIG. 2A can be restrained in a number of manners. For example, these may be formed within the lead body 12 during manufacture or these can be constrained by ribbing within the lead body 12 which is formed so as to flank the spacers and hold these therebetween. The spacers 24, 26 can also be formed to be of sufficient width to deter migration or collapse within the lead body 12. The spacers 24, 26 may also be formed as pairs of disks that are separated by a smaller diameter rod, which may be conductive or which may be hollow and filled with FCE 14, and the rod and pair of disks thereby form a spool. The lead for communicating electrical signals of FIG. 2A may be realized as a sheath having an electroconductive proximal lead connector and an electroconductive distal lead connector wherein the lead is contains at least one spacer element which defines at least a first compartment and a second compartment which are positioned serially within the sheath. The compartments are configured for jointly operating to provide electrical communication between the proximal and distal lead connector. The serial compartments may contain fluid and/or conductive elements and when fluid conductive elements are used the fluid can be fully restricted within each particular compartment. When one or more fluid compartments are defined these may be either non-pressurized or pressurized. By providing compartments, pressures due to bending of the lead can be isolated to a particular portion of the lead, rather than causing fluid to flow away from the source-point of the pressure, which may allow local twisting or kinking of the lead to occur. The spacer elements can also serve as support structures which prevent lead collapse and increases in fluid pressure due to external forces on the lead. The provision of compartments thereby improves performance by maintaining minimum and maximum pressures levels within a particular range, as compared to a design in which the internal lumen forms a single compartment along the length of the lead. Other methods of endoskeleton and exoskeleton structures also address issues related to both local and distributed sources of pressure, torque, kinking, and stretch.

Figure 2B:
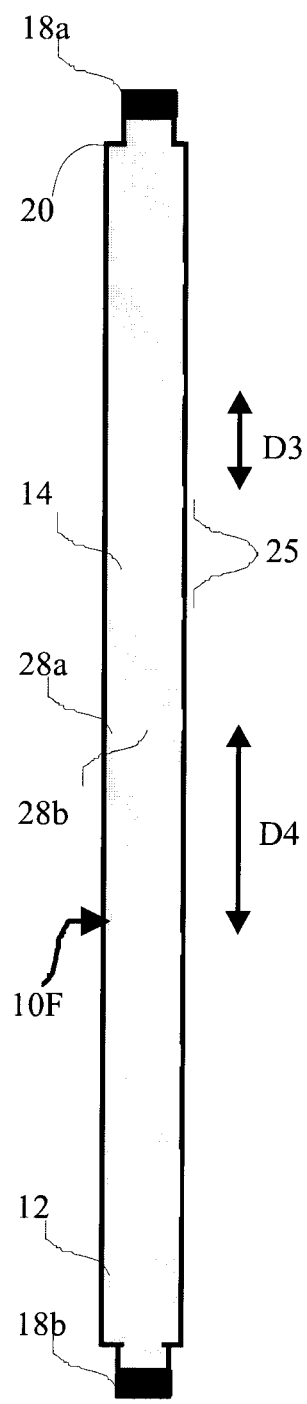
FIG. 2B is a schematic representation illustrating a lead comprising fluid compartments and non-conductive spacers.

FIG. 2B shows additional embodiment of the invention that is a lead 10F which is an alternative "serial" embodiment. In this embodiment at least two non-conductive spacer elements 28a and 28b are used to create conducting compartments 25 (as shown in FIG. 2A) which contain an FCE 14. Again, conducting compartments 25 can contain only FCEs, or can contain SCE 16 instead of, or in addition to the FCE 14. Additionally, the plurality of two or more non-conductive spacers 28a and 28b can be evenly distributed along the length of the lead body 12 or can have unique separations as indicated by D3 and D4 in the FIG. In this case, all the conductive spacers 28a contain gaps 28a in order to provide the FCE 14 to travel between compartments 25 and to enable conductive connectively throughout the lead body 12. While the conductive spacers 24, 26 can be considered as both a type of FCE 16 as well as a type of endoskeletal support, the non-conductive spacers only provide the latter function. The spacer elements closest to the proximal leads of FIGS. 2A,2B are relatively longer than the other spacers in order to show that these may be non-uniform, an in fact may each extend across even 10% or more of the total lead length.

Figure 3A:
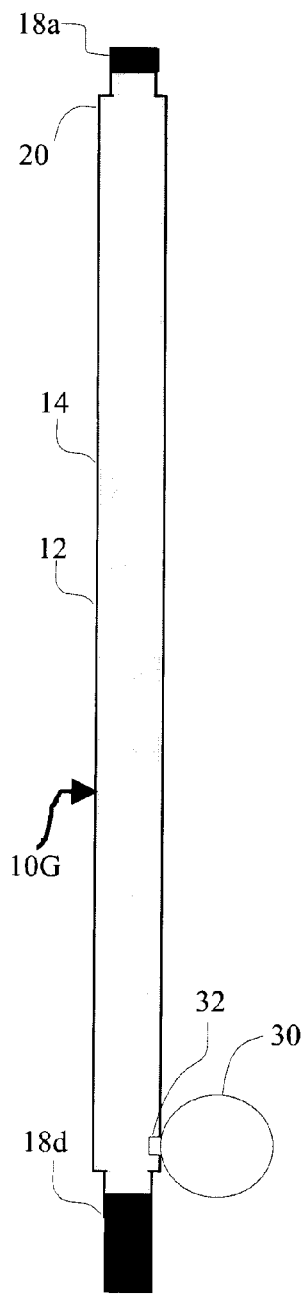
FIG. 3A is a schematic representation illustrating a lead comprising a fluid compartment a pressure regulator that is realized in the form of a reservoir and passage.
Figure 3B:
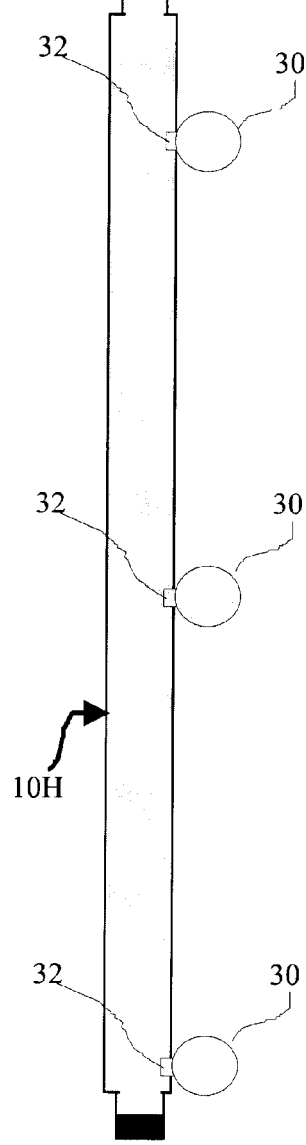
FIG. 3B is a schematic representation illustrating a lead comprised a fluid element and 3 pressure regulators.
Figure 3C:
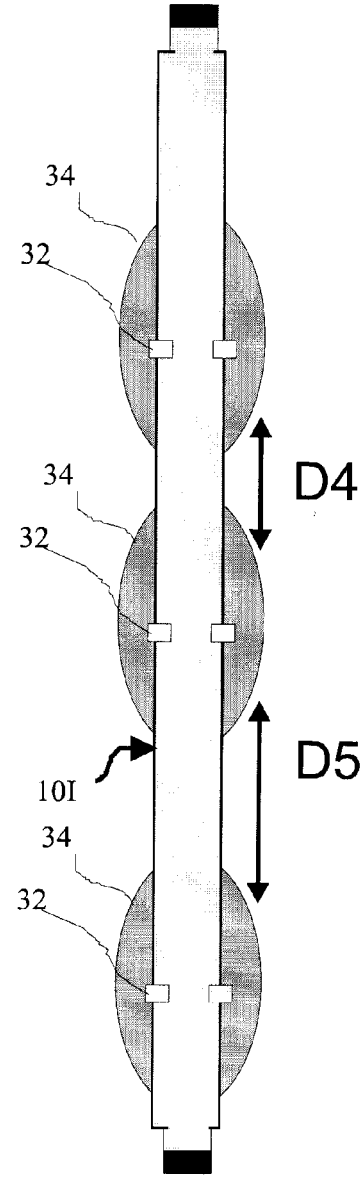
FIG. 3C is a schematic representation illustrating a lead comprised a fluid compartment and an exoskeleton comprising a series of circumferentially arranged reservoirs.

FIG. 3A shows additional embodiment of the invention that is a lead 10G in which a single FCE 14 conductive signals along the lead body 12. This embodiment also shows a pressure regulator 30 which may be in the form of a passive pressurized reservoir. The pressure regulator 30 can serve maintain the pressure of the lead body 12 so that this stays within a specified range when the electrode body 12 is stretched or flexed. The regulator 30 can be made of a flexible material which exerts a specified pressure on the FCE 14 via a passage 32 which may open or which may have a one way valve through which fluid may travel. Since the regulator 30 may be more flexible than the lead body 12, it may serve as a pressure release when the body is twisted. The regulator 30, may also serve to provide additional FCE when the lead 12 is stretched. FIG. 3B shows additional embodiment of the invention that is a lead 10H in which a single FCE 14 conductive signals along the lead body 12. This embodiment also shows a series of pressure regulators 30 which contain passages 32 which may be distributed along the reservoir in order to maintain localized pressurized within the reservoir. This may also be useful when more than one compartment 25 is provided within the lead, in which case the regulators 30, may serve to maintain different pressure levels. Rather than being formed cylindrically, which may cause problems during placement of the lead as it is guided through tissue, the regulators 30 may be formed as other shapes. FIG. 3C shows additional embodiment of the invention that is a lead 10I in which a single FCE 14 conducts signals along the lead body 12. This embodiment also shows a series of low-profile concentric pressure regulators 34 which contain passages 32 which may be distributed at distances such as D1 or D2 along the reservoir in order to maintain localized pressurized within the reservoir. The concentric pressure regulators here also serve as an exoskeleton that provides increased rigidity to the lead body 12. Exoskeletal support components such as these, which do not have to be realized as regulators, may flank the lead only across portions which will be especially exposed to bending forces such as when the lead extends across a bone or curves around tissue.

FIG. 4A shows additional embodiment of the invention that is a multi-stranded FCE lead in which a parallel leads 12 conduct signals along separate FCEs 14. The multiple leads 12 can be wrapped within a multi-lead sheath 40 which contains both the leads 12 and inter-lumen space 42 which in practice will be minimized, but which can also be filled with either a gas or liquid. These multiple strands can terminate at electrically isolated portions of the lead connectors in order to carry unique signals across the lead or can serve as a redundant system for carrying a single electrical signal. Alternatively, pairs of strands which are less likely to be simultaneously kinked (e.g. pairs located opposite each other) can carry a particular signal in a redundant fashion.

FIG. 4B shows an additional embodiment of the invention in which the lead body 12 contains a FCE 14, and in which an intra lead support matrix 44 is also provided. The intra-lead support matrix 44, may be comprising one or more supporting endoskeletal members, which in this case are a horizontal support 44a vertical support 44b. The supports 44 may be locally positioned and discontinuous or may extend along approximately the entire length of the lead body 12. In the latter case, the division of the FCE 14 permits either of two designs to be implemented. in a first design, the subdivisions of the FCE which are created by the supports 44 serve as parallel and independent signal conduction pathways, each of which terminates at separate distal lead connectors or a connector with electrically isolated portions 18e. Alternatively, the conduction pathways may serve as redundant pathways all of which terminate at a particular distal lead connector 18f (note: both 18e and 18f are illustrated as cross sectional schematic views).

FIG. 4C shows additional embodiment of the invention in which the lead body 12 contains a FCE 14, and in which an intra lead support matrix 44 is again provided, but which is now realized as having horizontal supports 44c and vertical supports 44d which suspend an intra-lead lumen 46 within the lead body 12. The intra-lead support matrix 44 deters the intra-lead lumen from resting against the lead body 12. The lead contains a separate fluid 14b which exists between the intra-lead lumen 46 within the lead body 12, This fluid 14b may be electrically, optically or thermally conductive or may have other properties and may be electrically non-conductive. The fluid 14b and may be contained within the body 12 at the same or different pressure as which the FCE 14 is contained within the intra-lead lumen 46.

FIG. 4D shows additional embodiment of the invention in which the lead body 12 contains a FCE 14, and in which an intra lead support matrix 44 is again provided, but which is now realized as having horizontal supports 44e and vertical supports 44f which suspend an intra-lead lumen 46 within the lead body 12, and which define an intra-lead space 48. The intra-lead space can contain air or a gas which may be pressurized, can contain a lubrication coating, or may contain other elements such as SCEs 16. It is understood that other embodiments, with the intra-lead space and intra-lead lumen contain other material are also possible, and each of these longitudinal pathways may be divided into serially located compartments.

FIG. 4E shows additional embodiment of the invention in which the lead body 12 contains a FCE 14, and in which an intra-lead rod matrix 50 is used within at least a portion of the body length. The intra-lead rod matrix 50 can comprise a rod member which may be made of conductive or non-conductive material and which may have a matrix throughout which the FCE 14 may reside. The intra-lead rod matrix 50 may be selected to provide an internal support, to constrain the flexibility of the lead 12, and to inhibit kinking of the lead 12 or other disruption to the continuity of the SCE 14 contained in the lead.

FIG. 5 shows an additional embodiment of the invention in which the FCE lead 10 is used as a connector between two conventional leads 60. Because the FCE lead 10 permits greater stretching and bending than conventional leads 60, the FCE lead 10 can be used to join the leads in an area with relatively increased movement. Interspersing conventional leads with an FCE lead can reduce the strain, flexibility requirements of the conventional leads 60. In the figure the FCE 10 is connected to conventional leads 60 using terminal connectors 19 which connect to connector 62 on the conventional lead 60 which are designed for this connection. In this embodiment the FCE lead 10 functions as an 'elastic bridge' between conventional leads 60. If the FCE lead 10 was only configured on its proximal lead connector for connection to a conventional lead 60, and was configured on its distal lead connector for connection to a device or to a sensor then the FCE 10 would function as an 'elastic terminal member'. In this manner conventional leads can be used for a relatively greater portion of the distance over which the signal must travel and the FCE 10 is used to provide increased elasticity compared to that which would be obtained using only conventional leads. This embodiment serves to decrease the strain which is provoked on conventional leads during use and can also be used to increase the subjective comfort of a patient since the elastic bridge or elastic terminal member allows greater movement without feeling as much 'pull' from implanted leads.

FIG. 6a shows an embodiment of the terminal connectors 18 which comprise a conductive contact 52a that is formed on a threaded connector 54 that connects to a terminal portion 56 which can be received by the terminal portion 20 of the lead 10. In FIG. 6B, the conductive contact 52b is both elongated and threaded for connection to other devices or leads rather than for contact with human tissue. An epoxy resin, or glue, may be used to form a non-leaking seal. Additionally, the terminal portions may be sealed completely and the threaded connector may have a needle that punctures the material to make contact with the conductive elements of the lead. When conductive spacer units are formed into the lead these may form water-tight seals which facilitates connection and leakage issues which may be encountered, for example, when a conductive fluid rather than gel is provided in the lead.

Transmission of Multiple Signal Modalities

The fluid based leads can also be used to conduct light, such as laser light, during the provision of therapy, or may conduct both light and electricity. When light is transmitted along the conduit the sheath may contain or be a lumen which is coated with a reflective material to provide suitable transmission as a waveguide which provides for sufficient internal reflection. The core, cladding, buffer, or jacket of the optical fiber conduit may primarily or completely be comprising transparent fluid which increases the flexibility of the lead. The core may also be made of a glass or plastic substrate which may be surrounded by a protective rail. An elastic lead may incorporate both a nanoStructures™ optical fiber design as well as a gel which may be used to provide simultaneous electrical transmission or increased elasticity. When light is transmitted along the lead then the terminal ends must be configured to allow light, or both light and electrical, signals to pass within the conduit. Gels that may be used either along the entire portion of the lead, in portions of the lead, or only at, or near, the lead terminals are those which provide good index-matching. Index matching gels are materials such as liquids, cements (adhesive), or gels, which has an index of refraction that closely approximates that of an optical element or fiber with which it is operating. Recently, new types of optical fiber have been developed that have interior microchannels oriented along their length, and these have been filled with fluids and examined as optical conduits (e.g., U.S. Pat. No. 7,110,646). In one embodiment a lead for optical signal communication is comprising a stretchable sheath containing an internal surface that is optically reflective and a fluid which is approximately transparent, a proximal lead connector with an optically transparent portion, a distal lead connector with an optically transparent portion, and at least one support structure for deterring unwanted deformation of the sheath from occurring. The lead for optical signal communication a can further be altered to also allow electrical signal transduction by using a fluid which is electroconductive such as an electrolyte. The fluid can provide both optical and electrical communication between the proximal and distal lead connector and can approximately conforming to the shapes which the sheath can assume. In this case the lead connectors must also have a portion which is electrically conductive so that both optical and electrical signals may be transmitted along the lead.

Functional Considerations

The various embodiments of the leads shown herein may be used to transmit electrical signals to accomplish a number of operations related to the provision of monitoring or therapy. The transmission characteristics, capacities, and limits will vary according to the characteristics of conductive mediums relied upon, including the conductivity of the material, the cross sectional area of lead body, and the length of the lead. In general, R is equal to L/CA, where R is the resistance, L is the cumulative length of the lead, C is the conductance of various fluids or solids materials used to provide electrical transmission, and A is the cross sectional area of the lead. This relationship is extendable to specific embodiments and can be used to design leads which are proportioned so that properties such as resistance and capacitance are within specified ranges. Likewise, the number of compartments 25 used, their cross sectional area, and their properties, such as capacitive capacities will alter the attenuation (e.g. low pass filtering) characteristics of the transmitted signals. Generally as the number of compartments increases, the functional lowpass filter of the lead may normally decrease in frequency. The length and circumference of a given lead can be selected in relation to the properties of the signal transmission for which the lead will be used, using the equation Rm=L/CA, where, Rm is the maximum allowable resistance level, L is the length of the lead, C is the lead capacitance; and, A is the cross-sectional lead area of the fluid conductive element. The characteristics of L, C, and A are maintained within selected limits to maintain the value of R below a specified level. C and A can both adjusted according to the characteristics of any endoskeletal elements of the design such as spacer elements.

When the lead is stretchable, the transmission of the signal may be altered based upon the amount the lead is stretched. Accordingly, strain or pressure gauges may be provided for the lead, or within the device, in order allow an implanted device to calibrate or adjust the transmitted potentials so that these are adjusted correctly for the associated amount of stretching. Proper lead design serves to minimize this type of variation so this type of adjustment is not normally needed.

Methods of Manufacture

A number methods of manufacture may be used during the formation of the leads described herein. In general, the aim of the manufacturing process is to produce a lead body or sheath that contains one or more FCEs and/or SCEs (which will be referred to simply as conductive elements or "CEs") that enable the lead to conduct signals along its entire length. The lead bodies may be formed and then filled with a CE using one or more steps, such as capillary action. Either the sheath material or CE can be heated or cooled and be biased under positive or negative forces of pressure. CE material may be drawn into one end of the lead body using suction applied to the opposite end, and this may be mechanically assisted from the outside of the sheath. The lead body may be coated or sprayed with a material which acts to harden or gel the CE. The CE can be initially drawn into the lead body while in a free-flowing fluid state and can then be transformed into a solid or gel. For example, the fluid CE can contact a transforming substance (e.g., a catalyst) that already resides in the sheath, and can thereby assume a more rigid state. Depending upon the design of the lead and the manufacturing processes that are relied upon, when the CEs include a wire which is surrounded by a gel, either of these components can exist within the sheath, prior to the application of the other. The sheath can be coated on its interior surface with a resin, a gel, a vapor deposited metal film or salt film prior to the introduction of the CE (e.g. a coated wire could be pulled through the length of the sheath to deposit this coating through physical contact).

The fluid leads of the current invention can be manufactured using one or more steps which are similar conventional methods which are used for manufacturing coated wires while a number of adjustments or modifications of these processes are also possible. The CE can be formed into a hardened "wire bar" form that is then pressed within an insulative sheath material to form the lead body. When the CE is mostly fluid, the wire form can be obtained by freezing the CE material prior to receiving its outer coat. When the CE is mostly a conductive powder, the wire form can also be obtained by pressing a fixed amount into a mold and applying pressure to create a compacted, yet possibly fragile wire bar (also a binding material may be added). The conductive powder can be finely-ground aluminum, which may have already been sifted using one or two filters. Aluminum dust is a good conductor and does not rust and would serve well in the fluid leads. When the powder is held together with a binder, this may also be electroconductive, and may be mixed within the powder itself or can be sprayed upon the outside of the bar. Alternatively, the binder can be sprayed to produce a first layer that stabilizes the conductive element's structure and this can then be dipped into a liquid sheathing material which then is permitted to dry.

In one step, a CE bar can be sprayed with a plurality of coatings which may form the lead's sheath (e.g., rubberized spray or vinyl lacquer may be painted on). Alternatively, this step in the process can be used to simply provide a support material in order to retain the bar's shape, or may be used to simply form a liner between the CE and the lead body. The plurality of coatings may each be of the same or different material.

Processes which involve the application of electrical current can also be used in the formation of the lead. For instance, electricity can be applied in order to densify, shrink, or cause crystal formation within the CE (e.g., sintering processes) at different points of the manufacturing process. Hammering of the CE material, prior to or after being coated may also be desirable in order to compact the CE further (e.g., Swaging processes can be used). In addition to mechanically-based deforming and binding techniques, other forces can also be used. For example, electromagnetic forming (EM forming or Magneforming) is a type of high energy rate metal forming process that uses pulsed power techniques to create ultrastrong pulsed magnetic fields to rapidly reshape metal parts. The technique is sometimes called high velocity forming. While normally used for sheet-type parts, the CE bars may exist as conductive sheets early on and these are later cut during a subsequent step of the manufacturing processes. At certain stages it may be necessary to anneal the CE material to allow further processing.

When the CE is a FCE which is a gel that has not yet solidified, during the manufacturing process electric, magnetic, and mechanical forces can be applied to the lead to increase the likelihood that the components of the gel will remain uniform during both manufacture and during subsequent use. For example, the lead may be rotated while a gel is hardened so that any conductive particulate remains homogenously dispersed within the gel-matrix and does not result in accumulation on the bottom inner surface of the lead due to gravity.

When in liquid form, the CE can be drawn into the conduit housing by immersing the housing and permitting the CE to be drawn in by capillary forces. Further, once filled, the conduits can be immersed in a fluid having greater saline, or other content, so that this is distributed into the CE through diffusion.

The filling process can occur in steps. For example, in the first step the conduit is filled with alcohol. In the second step, the alcohol is drawn off and the conduit is filled with distilled water. In the third step, the water is drawn out of one end in order to draw the CE into the conduit at its other end.

When in gel form, the CE can be placed into the housing of the conduit and then the conduit can be drawn, pulled in order to further shape the conduit, for example, in order to reduce its diameter and increase its length. This pulling can be done while the distal tips of the conduit are open or are sealed, and can also be done in a hot or cold temperature that is controlled. The total length of the conduit may then be clipped in order to utilize, for example, only the more centrally located length.

When the CE has a gel rather than fluid quality, rather than being isotonic, the CE can be configured to change in its conductivity along the length of the conduit, for example, being hypotonic at one end and hypertonic at the other. Likewise, when the tip of the conduit includes a gel, this gel can be hyper-tonic or hypo-tonic with the tissue or fluid of the body into which it is placed.

When the CE is a gel having a rubbery quality then the CE may be stretched or compressed either prior to, or subsequent to, being sheathed. Further, the gel may be heated or cooled in the relaxed, stretched, or compressed state in order to obtain various benefits. For example, freezing the gel in a compressed state would then allow the resulting bar to be removed from the compressive forces so that it may receive its sheath housing. While in the frozen state the bar may also be physically cut to reduce the diameter or length.

The leads of the current invention provide increased ductility and malleability both in terms of versatility of the leads and their shapes, as well as during use. The leads can have a multi-stranded structure, similar that which exists in 'multi-stranded wire', which is more correctly termed a cable.

A number of methods can be used to apply a sheath to the CE material. For example, the CE may be layered between 2 sheets which are pressed onto the CE with glue deposited on each side for affixing the two sides together, the lead is then cut on both outer edges and then the sheath material is honed to its final shape. The CEs first are covered with various insulating materials, such as cotton, rubber, or plastic, wrapped in concentric fashion and further protected with, substances such as paraffin, some kind of preservative compound, bitumen or lead sheathing or steel taping. The stranding or covering machines employed in this work can be designed to carry supplies of material and apply it to the CE as it is passing through the machine at a rapid rate. Machines for applying this inner covering can have a large drum, which grips the CE and moves it through toothed gears at a definite speed; the CE passes through the centre of disks mounted above a long bed, and the disks carry a number of bobbins varying from, for example, 4 to 12 or more. A supply of covering material is wound on each bobbin, and the end is led on to the CE, which occupies a central position relatively to the bobbins; the latter being revolved at a suitable speed so that, the insulative material is consequently served to the CE, and may be wound in spiral fashion so as to cause overlap of material dispensed from different bobbins. If a large number of insulative strands are required, or multiple layers are to be applied, then the disks can be duplicated, so that 40 to 120 spools are carried, the latter sets of strands being laid over the first.

Further covering of the CE or the initial insulative layers may be accomplished by passing these through grooved rollers simultaneously with rubber strips located above and below, so that the rubber is crushed on to the existing leads, and this may emerge as a wide band. The separate leads are then parted forcibly, each retaining its rubber sheathing. Vulcanizing may be done afterwards in steam-heated drums. Many other methods exist for tubing manufacture including seamless, as-welded, and drawn-over-mandrel methods.

Additional auxiliary steps can be used in connection with lead and sheath manufacture, including preparation of the sheath material (e.g. plastic, polymers, rubber), cutting it into strips, and applying it to the lead as well as winding, weaving, and measuring the lengths of the conductive elements themselves.

The term "fluid", as used herein, can refer to a liquid, fluid, paste, or gel. Fluid can refer to a fluid which is contained in a gel. The fluid may be an electrolyte, such as chemically pure salt (KCL, NACL) diluted into triply distilled water. The fluid may be conductive or may be non-conductive and may contain conductive particles, alloys, powders, flakes, or composites which serve to provide or increase the conductivity of the fluid. Nano-engineered particles such as those containing fractal surfaces, or which are otherwise patterned may be suspended in the fluid. The fluid can include carbon nanotube-ionic liquid gels ("bucky" gels); electroconductive biocompatible hydrogel; silicone gel having a combination of conductive particles; gel with particles comprising silver coated mica or oxide free silver flakes. The fluids can be a relatively non-flowing gel or a flowing gel. Preferably the gel that is utilized is thermally stable at body temperatures. The fluid can be a salt-free and/or chloride-free gel (e.g., spectra 360 or LECTRON 11 electrode gel) saline electrode gel (Signal gel). The fluid can contain one or more of the following: water; alcohol; glycerol, sodium or potassium acetate; salts; NaCL; or KCL. The conductors can include materials described in fluids and gels, as well as solute or particulate matter which may function well to provide wanted characteristics such as electrical transmission are described in U.S. Pat. Nos. 5,348,686 to Vyas; 5,075,038 to Cole; 4,406,827 to Carim; 4,845,457 to Nakanishi; 5,178,143 to Kwak; 5,539,039 to Kwak; 5,645,062 to Anderson; 5,099,855 to Yount; 5,143,071 to Keusch. 4,016,869; 3,998,215; 3,989,050; 3,658,726; 3,265,638; and 4,406,827. These also describe saturated solutions, aqueous solutions, gels, electrical conductive gels, thickening agents, stabilizing agents, gums, conducting agents, resins, particles, pastes, conductive mediums, salts, thickening agents, electrolytes, and creams that may be utilized in the present invention.

The presently described embodiments of the lead systems and methods offer advantages over prior art. Although modifications and changes may be suggested by those skilled in the art, it is the intention of the inventor to embody within the patent warranted herein all changes and modifications as reasonably and properly come within the scope of their contribution to the art. The titles, headings, and subheadings provided in this specification are provided for organizational purposes only and are not meant to restrict the invention in any way, nor to limit material described in one section from applying to another section as would be apparent to those skilled in the art. In the drawings, the orientation, scale, and relative relationship of the components of the invention are not meant to be unduly limiting and additional types of embodiment and coaxial layers are possible. All prior art including patents, patent applications, and scientific references which are cited herein are incorporated by reference as if fully recited herein.

SCIENTIFIC REFERENCES

Liem L K; Simard J M; Song Y; and Tewari K. The patch clamp technique. Neurosurgery. 1995; 36: 382-92.

Lipton M J, Ream A K, Hyndman B H. A conductive catheter to improve patient safety during cardiac catheterization. Circulation. 1978 December; 58(6):1190-5.

Neher E, Sakmann B. Noise analysis of drug induced voltage clamp currents in denervated frog muscle fibres. J Physiol. 1976 July; 258(3):705-29.

Ream A K, Lipton M J, Hyndman B H. Reduced risk of cardiac fibrillation with use of a conductive catheter. Ann Biomed Eng. 1977 September; 5(3):287-301.

We claim:

1. A lead for communicating electrical signals, comprising:
   a. a sheath having an electrically conductive fluidic composition contained therein;
   b. an electroconductive proximal lead connector;
   c. an electroconductive distal lead connector;
   d. at least a first compartment and a second compartment being defined by at least one spacer formed within said sheath, said first and second compartments electrically connected together, containing said electrically conductive fluidic composition and positioned serially within the sheath, said compartments configured for operating jointly to provide serial electrical communication between the proximal and distal lead connectors.

2. The lead of claim 1, wherein said at least one spacer is electrically conductive, said spacer residing between the at least one first compartment and second compartment.

3. The lead of claim 1, wherein said at least one spacer contains a gap which allows a conductive fluid to flow through the at least first and second compartments.

4. The lead of claim 1 wherein at least one compartment is pressurized.

5. The lead of claim 1 further including at least a third compartment and a fourth compartment positioned in substantial alignment each with respect to the other within the sheath, said compartments configured for operating jointly to provide at least a second serial electrical communication between an electrode contact and the proximal lead connector.

6. A lead for communicating electrical signals, comprising:
   a. a sheath;
   b. an electroconductive proximal lead connector;
   c. an electroconductive distal lead connector;
   e. a conductive mixture contained within at least one compartment of said sheath for providing electrical communication between the proximal and distal lead connector and for approximately conforming to the shapes which the sheath can assume; and,
   f. at least one support structure mounted substantially perpendicular to an axis line of said sheath, said support structure defining a plurality of support elements for modulating deformation of the sheath.

7. The lead of claim 6 wherein at least one of the proximal lead connector and the distal lead connector is configured for connection to a conventional lead, whereby the lead acts as an elastic terminal member.

8. The lead of claim 6 wherein the sheath is modulated to provide an electrical resistance of said sheath to be less than 20% above the electrical resistance of said sheath when taken with respect to said sheath being devoid of kinking, twisting, or being in a collapsed state.

9. The lead of claim 6 wherein said support structure is an endoskeletal support structure located within the sheath.

10. The lead of claim 9 wherein the endoskeletal support is a spacer which contains a gap, said gap permitting flow of the conductive mixture along the length of the sheath.

11. The lead of claim 9 wherein the endoskeletal support transverses approximately the entire length of the sheath.

12. The lead of claim 9 wherein the at least one compartment for providing electrical communication between the proximal and distal lead connectors is configured to provide at least 2 channels along which electrical signals may travel and is also configured to provide redundant transmission of a single electrical signal being sent from the distal lead connector to the proximal lead connector, and said distal lead connector is configured with at least 2 electrically isolated contacts.

13. The lead of claim 9 wherein the at least one compartment for providing electrical communication between the proximal and distal lead connectors configured to provide isolated and independent transmission of at least two electrical signals between the distal lead connector and the proximal lead connector, and said distal lead connector is configured with at least 2 electrically isolated contacts.

14. The lead of claim 6 wherein said support structure is an exoskeletal support structure that resides primarily outside the sheath.

15. The lead of claim 6 wherein the conductive mixture is a fluid conductive element that is at least one of: a saline based fluid; a fluid containing electroconductive particles; a fluid containing metallic particles; a fluid containing nano-engineered particles.

16. The lead of claim 6 in which the conductive mixture is a fluid conductive element which is configured to be safe for use in MRI environments and the lead is further configured for attachment to an MRI safe implantable device.

* * * * *